United States Patent
Tao et al.

(10) Patent No.: US 6,197,294 B1
(45) Date of Patent: Mar. 6, 2001

(54) CELL SURFACE MOLECULE-INDUCED MACROPHAGE ACTIVATION

(75) Inventors: Weng Tao, Lincoln; Shou Wong, Cumberland, both of RI (US); William F. Hickey, Lyme, NH (US); Joseph P. Hammang, Barrington, RI (US); E. Edward Baetge, St. Sulpice (CH)

(73) Assignee: Neurotech S.A., Evry (FR)

( * ) Notice: Subject to any disclaimer, the term of this patent is extended or adjusted under 35 U.S.C. 154(b) by 0 days.

(21) Appl. No.: 09/178,869

(22) Filed: Oct. 26, 1998

(51) Int. Cl.[7] .......................... C07H 21/04; C12N 15/85; C12N 15/63; C12N 15/86; A61K 35/00

(52) U.S. Cl. .................. 424/93.21; 435/325; 435/320.1; 435/352; 435/354; 536/23.1; 536/23.4; 424/93.1; 424/93.2

(58) Field of Search .................................. 536/23.1, 23.4; 435/320.1, 325, 328, 352, 354; 424/93.1, 93.2, 93.21

(56) References Cited

FOREIGN PATENT DOCUMENTS

| 95/33828 | 2/1995 | (WO) . |
|---|---|---|
| 95/27042 | 10/1995 | (WO) . |
| 95/35120 | 12/1995 | (WO) . |
| 96/06165 | 2/1996 | (WO) . |
| WO 96/02646 | 2/1996 | (WO) . |
| 96/06642 | 3/1996 | (WO) . |
| 96/14397 | 5/1996 | (WO) . |
| 96/21466 | 7/1996 | (WO) . |
| 90/12035 | 4/1997 | (WO) . |
| 97/11607 | 4/1997 | (WO) . |

OTHER PUBLICATIONS

McGeer & McGeer, "The future use of complement inhibitors for the treatment of neurological diseases." Drugs 55(6):739–46, 1998.

Morgan et al., "The role of complement in disorders of the nervous system." Immunopharmacology 38(1–2):43–50, 1997.

Naka et al., "Complement activation as a cause for primary graft failure in an isogeneic rat model of hypothermic lung preservation and transplantation." Transplantation 64(9):1248–55, 1997.

Shen et al., "Characterization of neuronal cell death induced by complement activation." Brain Res Brain Res Protoc 1(2):186–94, 1997.

Shen et al., "Neuronal expression of mRNAs for complement proteins of the classical pathway in Alzheimer brain." Brain Res 769(2):391–5, 1997.

Tao et al., "Monomeric bovine IgG2 is a potent stimulus for bovine neutrophils." J Leukoc Biol, 58: 203–8, 1995.

Terai et al., "Neurons express proteins of the classical complement pathway in Alzheimer disease." Brain Res 769(2):385–90, 1997.

Gajewski et al, *Tumor rejection requires a CTLA4 Ligand provided by the host or expressed on the tumor: superiority of B7–1 over B7 for active tumor immunization*. 156(8) J. Immunol. 2909–17 (1996).

Stabila et al., *Cell surface expression of a human IgG Fc chimera activates macrophages through Fc receptors*. 16(13) Nat Biotechnol. 1357–60 (1998).

Yu et al., *The role of B7–CD28 co–stimulation in tumor rejection*. 10(6) Int. Immunol. 791–7 (1998).

Primary Examiner—John L. LeGuyader
Assistant Examiner—Michael C. Wilson
(74) Attorney, Agent, or Firm—Mintz,Levin,Cohn,Ferris, Glovsky and Popeo, P.C.; Ivor R. Elrifi; John Prince

(57) ABSTRACT

This invention provides cells containing recombinant polynucleotides coding for cell surface molecules that, when expressed in the cell, result in rejection of the cell by the host immune system. The invention also provides methods of using such cells, and capsules for delivery of biologically active molecules to a patient.

6 Claims, 5 Drawing Sheets

SEQUENCE LISTING

```
<160> NUMBER OF SEQ ID NOS: 14

<210> SEQ ID NO 1
<211> LENGTH: 1019
<212> TYPE: DNA
<213> ORGANISM: Homo sapiens
<220> FEATURE:
<221> NAME/KEY: gene
<222> LOCATION: ()..)
<223> OTHER INFORMATION: Description of Sequence: Recombinant
      Polynucleotide
<220> FEATURE:
<221> NAME/KEY: CDS
<222> LOCATION: (16)..(1008)

<400> SEQUENCE: 1
cccgaattcg ccacc atg atg gat caa gct aga tca gca ttc tct aac ttg       51
                Met Met Asp Gln Ala Arg Ser Ala Phe Ser Asn Leu
                  1               5                  10 ttt ggt gga gaa cca ttg tca tat acc cgg ttc agc ctg gct cgg caa      99
Phe Gly Gly Glu Pro Leu Ser Tyr Thr Arg Phe Ser Leu Ala Arg Gln
         15                  20                  25
```

```
gta gat ggc gat aac agt cat gtg gag atg aaa ctt gct gta gat gaa      147
Val Asp Gly Asp Asn Ser His Val Glu Met Lys Leu Ala Val Asp Glu
     30                  35                  40 gaa gaa aat gct gac aat aac aca aag gcc aat gtc aca aaa cca aaa      195
Glu Glu Asn Ala Asp Asn Asn Thr Lys Ala Asn Val Thr Lys Pro Lys
 45                  50                  55                  60 agg tgt agt gga agt atc tgc tat ggg act att gct gtg atc gtc ttt      243
Arg Cys Ser Gly Ser Ile Cys Tyr Gly Thr Ile Ala Val Ile Val Phe
                 65                  70                  75 ttc ttg att gga ttt atg att ggc tac ttg ggc tat tgt aaa ggg gta      291
Phe Leu Ile Gly Phe Met Ile Gly Tyr Leu Gly Tyr Cys Lys Gly Val
             80                  85                  90 gaa cca aaa act gag gga tcc gag ccc aaa tct tgt gac aaa act cac      339
Glu Pro Lys Thr Glu Gly Ser Glu Pro Lys Ser Cys Asp Lys Thr His
         95                  100                 105 aca tgc cca ccg tgc cca gca cct gaa ctc ctg ggg gga ccg tca gtc      387
Thr Cys Pro Pro Cys Pro Ala Pro Glu Leu Leu Gly Gly Pro Ser Val
    110                 115                 120 ttc ctc ttc ccc cca aaa ccc aag gac acc ctc atg atc tcc cgg acc      435
Phe Leu Phe Pro Pro Lys Pro Lys Asp Thr Leu Met Ile Ser Arg Thr
125                 130                 135                 140 cct gag gtc aca tgc gtg gtg gtg gac gtg agc cac gaa gac cct gag      483
Pro Glu Val Thr Cys Val Val Val Asp Val Ser His Glu Asp Pro Glu
                145                 150                 155 gtc aag ttc aac tgg tac gtg gac ggc gtg gag gtg cat aat gcc aag      531
Val Lys Phe Asn Trp Tyr Val Asp Gly Val Glu Val His Asn Ala Lys
            160                 165                 170 aca aag ccg cgg gag gag cag tac aac agc acg tac cgt gtg gtc agc      579
Thr Lys Pro Arg Glu Glu Gln Tyr Asn Ser Thr Tyr Arg Val Val Ser
        175                 180                 185 gtc ctc acc gtc ctg cac cag gac tgg ctg aat ggc aag gag tac aag      627
Val Leu Thr Val Leu His Gln Asp Trp Leu Asn Gly Lys Glu Tyr Lys
    190                 195                 200 tgc aag gtc tcc aac aaa gcc ctc cca gcc ccc atc gag aaa acc atc      675
Cys Lys Val Ser Asn Lys Ala Leu Pro Ala Pro Ile Glu Lys Thr Ile
205                 210                 215                 220 tcc aaa gcc aaa ggg cag ccc cga gaa cca cag gtg tac acc ctg ccc      723
Ser Lys Ala Lys Gly Gln Pro Arg Glu Pro Gln Val Tyr Thr Leu Pro
                225                 230                 235 cca tcc cgg gat gag ctg acc aag aac cag gtc agc ctg acc tgc ctg      771
Pro Ser Arg Asp Glu Leu Thr Lys Asn Gln Val Ser Leu Thr Cys Leu
            240                 245                 250 gtc aaa ggc ttc tat ccc agc gac atc gcc gtg gag tgg gag agc aat      819
Val Lys Gly Phe Tyr Pro Ser Asp Ile Ala Val Glu Trp Glu Ser Asn
        255                 260                 265 ggg cag ccg gag aac aac tac aag acc acg cct ccc gtg ctg gac tcc      867
Gly Gln Pro Glu Asn Asn Tyr Lys Thr Thr Pro Pro Val Leu Asp Ser
    270                 275                 280 gac ggc tcc ttc ttc ctc tac agc aag ctc acc gtg gac aag agc agg      915
Asp Gly Ser Phe Phe Leu Tyr Ser Lys Leu Thr Val Asp Lys Ser Arg
285                 290                 295                 300 tgg cag cag ggg aac gtc ttc tca tgc tcc gtg atg cat gag gct ctg      963
Trp Gln Gln Gly Asn Val Phe Ser Cys Ser Val Met His Glu Ala Leu
                305                 310                 315 cac aac cac tac acg cag aag agc ctc tcc ctg tct ccg ggt aaa          1008
His Asn His Tyr Thr Gln Lys Ser Leu Ser Leu Ser Pro Gly Lys
            320                 325                 330 tgaagcttgg g                                                         1019
```

```
<210> SEQ ID NO 2
<211> LENGTH: 331
<212> TYPE: PRT
<213> ORGANISM: Homo sapiens

<400> SEQUENCE: 2

Met Met Asp Gln Ala Arg Ser Ala Phe Ser Asn Leu Phe Gly Gly Glu
 1               5                  10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Gly Ser Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 3
<211> LENGTH: 974
<212> TYPE: DNA
<213> ORGANISM: Homo sapiens
<220> FEATURE:
<223> OTHER INFORMATION: Description of Sequence: Recombinant
      Polynucleotide
<220> FEATURE:
```

```
<221> NAME/KEY: CDS
<222> LOCATION: (16)..(963)

<400> SEQUENCE: 3
cccgaattcg ccacc atg atg gat caa gct aga tca gca ttc tct aac ttg         51
                Met Met Asp Gln Ala Arg Ser Ala Phe Ser Asn Leu
                 1               5                  10 ttt ggt gga gaa cca ttg tca tat acc cgg ttc agc ctg gct cgg caa           99
Phe Gly Gly Glu Pro Leu Ser Tyr Thr Arg Phe Ser Leu Ala Arg Gln
         15                  20                  25 gta gat ggc gat aac agt cat gtg gag atg aaa ctt gct gta gat gaa          147
Val Asp Gly Asp Asn Ser His Val Glu Met Lys Leu Ala Val Asp Glu
 30                  35                  40 gaa gaa aat gct gac aat aac aca aag gcc aat gtc aca aaa cca aaa          195
Glu Glu Asn Ala Asp Asn Asn Thr Lys Ala Asn Val Thr Lys Pro Lys
 45                  50                  55                  60 agg tgt agt gga agt atc tgc tat ggg act att gct gtg atc gtc ttt          243
Arg Cys Ser Gly Ser Ile Cys Tyr Gly Thr Ile Ala Val Ile Val Phe
                 65                  70                  75 ttc ttg att gga ttt atg att ggc tac ttg ggc tat tgt aaa ggg gta          291
Phe Leu Ile Gly Phe Met Ile Gly Tyr Leu Gly Tyr Cys Lys Gly Val
             80                  85                  90 gaa cca aaa act gag gga tcc gca cct gaa ctc ctg ggg gga ccg tca          339
Glu Pro Lys Thr Glu Gly Ser Ala Pro Glu Leu Leu Gly Gly Pro Ser
         95                 100                 105 gtc ttc ctc ttc ccc cca aaa ccc aag gac acc ctc atg atc tcc cgg          387
Val Phe Leu Phe Pro Pro Lys Pro Lys Asp Thr Leu Met Ile Ser Arg
    110                 115                 120 acc cct gag gtc aca tgc gtg gtg gtg gac gtg agc cac gaa gac cct          435
Thr Pro Glu Val Thr Cys Val Val Val Asp Val Ser His Glu Asp Pro
125                 130                 135                 140 gag gtc aag ttc aac tgg tac gtg gac ggc gtg gag gtg cat aat gcc          483
Glu Val Lys Phe Asn Trp Tyr Val Asp Gly Val Glu Val His Asn Ala
                145                 150                 155 aag aca aag ccg cgg gag gag cag tac aac agc acg tac cgt gtg gtc          531
Lys Thr Lys Pro Arg Glu Glu Gln Tyr Asn Ser Thr Tyr Arg Val Val
            160                 165                 170 agc gtc ctc acc gtc ctg cac cag gac tgg ctg aat ggc aag gag tac          579
Ser Val Leu Thr Val Leu His Gln Asp Trp Leu Asn Gly Lys Glu Tyr
        175                 180                 185 aag tgc aag gtc tcc aac aaa gcc ctc cca gcc ccc atc gag aaa acc          627
Lys Cys Lys Val Ser Asn Lys Ala Leu Pro Ala Pro Ile Glu Lys Thr
    190                 195                 200 atc tcc aaa gcc aaa ggg cag ccc cga gaa cca cag gtg tac acc ctg          675
Ile Ser Lys Ala Lys Gly Gln Pro Arg Glu Pro Gln Val Tyr Thr Leu
205                 210                 215                 220 ccc cca tcc cgg gat gag ctg acc aag aac cag gtc agc ctg acc tgc          723
Pro Pro Ser Arg Asp Glu Leu Thr Lys Asn Gln Val Ser Leu Thr Cys
                225                 230                 235 ctg gtc aaa ggc ttc tat ccc agc gac atc gcc gtg gag tgg gag agc          771
Leu Val Lys Gly Phe Tyr Pro Ser Asp Ile Ala Val Glu Trp Glu Ser
            240                 245                 250 aat ggg cag ccg gag aac aac tac aag acc acg cct ccc gtg ctg gac          819
Asn Gly Gln Pro Glu Asn Asn Tyr Lys Thr Thr Pro Pro Val Leu Asp
        255                 260                 265 tcc gac ggc tcc ttc ttc ctc tac agc aag ctc acc gtg gac aag agc          867
Ser Asp Gly Ser Phe Phe Leu Tyr Ser Lys Leu Thr Val Asp Lys Ser
    270                 275                 280 agg tgg cag cag ggg aac gtc ttc tca tgc tcc gtg atg cat gag gct          915
Arg Trp Gln Gln Gly Asn Val Phe Ser Cys Ser Val Met His Glu Ala
```

```
                285                 290                 295                 300
ctg cac aac cac tac acg cag aag agc ctc tcc ctg tct ccg ggt aaa            963
Leu His Asn His Tyr Thr Gln Lys Ser Leu Ser Leu Ser Pro Gly Lys
                    305                 310                 315 tgaagcttgg g                                                                974

<210> SEQ ID NO 4
<211> LENGTH: 316
<212> TYPE: PRT
<213> ORGANISM: Homo sapiens

<400> SEQUENCE: 4

Met Met Asp Gln Ala Arg Ser Ala Phe Ser Asn Leu Phe Gly Gly Glu
 1               5                  10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Gly Ser Ala Pro Glu Leu Leu Gly Gly Pro Ser Val Phe Leu Phe
            100                 105                 110

Pro Pro Lys Pro Lys Asp Thr Leu Met Ile Ser Arg Thr Pro Glu Val
        115                 120                 125

Thr Cys Val Val Asp Val Ser His Glu Asp Pro Glu Val Lys Phe
    130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
    210                 215                 220

Asp Glu Leu Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Lys Leu Thr Val Asp Lys Ser Arg Trp Gln Gln
        275                 280                 285

Gly Asn Val Phe Ser Cys Ser Val Met His Glu Ala Leu His Asn His
    290                 295                 300

Tyr Thr Gln Lys Ser Leu Ser Leu Ser Pro Gly Lys
305                 310                 315

<210> SEQ ID NO 5
<211> LENGTH: 33
```

```
<212> TYPE: DNA
<213> ORGANISM: Artificial Sequence
<220> FEATURE:
<223> OTHER INFORMATION: Description of Artificial Sequence: Primer

<400> SEQUENCE: 5
cccggatccg cctccaccaa gggcccatgc gtc                              33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 6
cccaagcttc atttacccgg agacaggag agg                               33

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
cccggatccg ccaccatgat ggatcaagct ag                               32

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 8
cccgaattcg ccaaaacgac accccatct g                                 31

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 9
cccaagcttc atttaccagg agagtgggag ag                               32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 10
cccgaattcg ccaccatgat ggatcaagct ag                               32

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
```

-continued

```
tgtccttttg gcctcagttt ttggttctac                                              30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
ccaaaaactg aggccaaaac gacaccccca                                              30

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 13
cccgaattcg ccaccatgat ggatcaagct ag                                           32

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
gtgtgcacac cgctggacag ggatccagag                                              30
```

CELL SURFACE MOLECULE-INDUCED MACROPHAGE ACTIVATION

TECHNICAL FIELD OF THE INVENTION

This invention relates generally to the immunoglobulins, and more particularly to a cell surface molecule-induced macrophage activation that results in the rejection by the host of the cell expressing the cell surface molecule.

BACKGROUND OF THE INVENTION

Cell therapy seeks to provide biologically active molecules to a patient by implanting cells that produce the biologically active molecules into the patient. In unencapsulated cell therapy approaches, "naked" cells are implanted. Several approaches have been taken to prevent rejection of the implanted "naked" cells. Treatments include immunosuppression of the patient, preclearance from the recipient serum of natural antibodies, or administration of high doses of low molecular weight haptens to inhibit natural antibody binding to transplanted tissue. Alternatively, researchers have proposed the alteration of cells to reduce or eliminate expression of antigen or epitopes that stimulate rejection of the cells or tissue by natural antibodies in a recipient. However, using mitotically active cells creates a risk of tumorigenicity of the implanted tissue.

In encapsulated cell therapy approaches, a permselective physical barrier immunoisolates the implanted tissue from the host tissue. The barrier permits passage of the desired molecules between the patient and the encapsulated tissue, but protects the encapsulated cells or tissue from destruction by the immune system of the patient. Use of xenogeneic tissue or cells in encapsulated cell therapy also acts as a "safety feature," because encapsulated cells are rejected by the patient's immune system if the capsule breaks or ruptures.

A patient's immune system has several components, some of which are useful for encapsulated cell therapy and some of which are undesirable. In one component, phagocytes scavenge target cells, such as the xenogeneic cells described above. In particular, antibody-dependent cell-mediated cytotoxicity (ADCC) has an important role in the destruction of many target cells, including tumor cells, by macrophages. Opsonization of target cells with immunoglobulin G (IgG) enhances the removal of these materials from a host. The role of macrophages in the destruction of target cells by ADCC in the presence of specific antibodies has been well established. While the selectivity of macrophage targeting is based on antibody specificity, the lytic attack on the target cells is triggered by Fc receptor-mediated ADCC.

Another component of the immune system is the activation of the complement system. The two pathways of complement activation (the classical and the alternative pathways) are both directed at a central step in complement activation, the cleavage of C3. A single terminal pathway is the formation of a membrane attack complex (MAC). The classical pathway is normally activated by antigen-antibody complexes., where certain antibodies are complement fixing (capable of binding to complement to cause activation of the classical pathway). Activation of the classical pathway can be initiated with binding of C1q, the first factor of complement cascade, to the Fc region of immunoglobulin. Then, a cascade of proteolytic events results in the activation of C5 convertase, which cleaves C5 into C5b and C5a. The C5b then binds C6, C7, C8 to form a C5b-8 complex. Binding of C9 molecules to C5b-8 forms C5b-9 (the MAC), which inserts into lipid bilayers and forms transmembrane channels that permit bidirectional flow of ions and macromolecules. By this mechanism, complement causes lysis of the cells.

The complement system is important in host defense, but activation at inappropriate sites or to an excessive degree can cause host tissue damage. Complement is a factor in the causation or propagation of tissue injury in numerous diseases. For encapsulated cell therapy approaches in humans, therefore, (1) unencapsulated cells should be rejected immediately by the host; (2) encapsulated cells should be non-immunogenic to the host; and (3) the cell elimination process should not lead to immunological memory of the host. Accordingly, it would be desirable to be able to deliver a biologically active molecule to human patients using encapsulated cells or tissue that both have a human immunological "background," but also provide the safety feature of rejection by the patient in the event of capsule rupture or failure.

SUMMARY OF THE INVENTION

The invention provides novel approaches for expressing naturally type I cell surface molecules (i.e., with the carboxy terminus [C-terminus] projecting toward the cytosol and the amino-terminus [N-terminus] projecting away from the cell surface) as type II molecules (i.e., with the N-terminus projecting toward the cytosol and the C-terminus projecting away from the cell surface). The biological function is maintained in the type II orientation. Using this approach (1) cells expressing such molecules can be used as therapeutic agents and (2) a screening process can evaluate the function of novel molecules that were not previously available for testing. The invention also provides a novel approach to predetermining the fate of the transformed cells. Thus, the invention is new aspect of gene therapy and tumor therapy. While gene therapy is a new field, conferring cytotoxic sensitivity on tumor cells has been an area of active research. The strategy described here can be used to target tumor cells; tumor cells expressing immunostimulatory cell surface polypeptides are therefore more susceptible to macrophage clearance.

The invention provides novel immunostimulatory cell surface polypeptides, novel recombinant polynucleotides encoding immunostimulatory cell surface polypeptides, and transformed cells containing the recombinant polynucleotides. When a transformed cell containing a recombinant polynucleotide expresses the encoded immunostimulatory cell surface polypeptide in a host, the host undergoes an immune response that results in rejection of the transformed cell by the host. The host immune response can include the activation of phagocytes, such as macrophages, but does not include complement fixation. In a specific embodiment, the immunostimulatory cell surface polypeptides is a chimeric polypeptide containing the human transferrin receptor membrane domain anchors a human $IgG_1$ Fc to the surface of the cell plasma membrane in a "reversed orientation," thus mimicking the configuration of IgG during opsonization. The transformed cells containing the recombinant polynucleotides of the invention are therapeutically useful for the treatment of many disorders.

The invention also provides diagnostic methods for identifying novel therapeutics. In one embodiment, the invention is a method for testing phagocytes for response to an immunostimulatory cell surface polypeptide. A phagocyte is contacted in vitro with a transformed cell containing a recombinant polynucleotide. The recombinant polynucleotide is a promoter operably linked with a polynucleotide coding for an immunostimulatory cell surface polypeptide, and the immunostimulatory cell surface polypeptide activates phagocytes, but does not fix complement. The phagocytic activity of the phagocyte is compared with control phagocyte; and increased phagocytic activity indicates that the phagocyte responds to the immunostimulatory cell surface polypeptide. In another embodiment, the invention is a method for identifying a compound that modulates phagocyte response to an immunostimulatory cell surface polypeptide. A phagocyte is contacted in vitro with a transformed cell containing a recombinant polynucleotide. The process is then repeated by contacting a phagocyte in vitro with a test compound and the transformed cell containing a recombinant polynucleotide. The phagocytic activity of the phagocyte in the absence of the test compound is compared with the phagocytic activity of the phagocyte in the presence of the test compound. A change in the phagocytic activity indicates that the test compound modulates phagocyte response to the immunostimulatory cell surface polypeptide.

The invention further provides a method for stimulating phagocyte activity. A transformed cell containing a recombinant polynucleotide containing a promoter operably linked with a polynucleotide coding for an immunostimulatory cell surface polypeptide is administered to a host. In one embodiment, the stimulated phagocyte is a macrophage, especially a macrophagic tumor cell. In another embodiment, the transformed cell contains a therapeutic compound, such as an anti-tumor compound.

The invention provides a method for modulating an immune response in a host. A transformed cell containing a recombinant polynucleotide with a promoter operably linked with a polynucleotide coding for an immunostimulatory cell surface polypeptide is administered to the host. The administration stimulates an immune response to the transformed cell, because the activation of phagocytes, especially macrophages, acts to regulate both T and B lymphocytes. Macrophages engulf the transformed cell and present the antigenic determinants from the transformed cell to T cells, stimulating an immune response. In one embodiment, the cell expresses, on the cell surface, a "second antigen," such that the host produces an immune response against the second antigen from the transformed cell. The immunostimulatory cell surface polypeptide enhances the cellular interaction with macrophages. As a result of this enhanced cellular interaction, the second antigen is presented as a target for T-cells. In one embodiment, the transformed cell expresses the second antigen from a recombinant polynucleotide.

The invention provides a method for ablating undesirable target cells, such as tumor cells in a patient, by the targeted delivery of the recombinant polynucleotides of the invention followed by either constitutive or inducible expression of encoded polypeptide. The delivery of the immunostimulatory cell surface polypeptide of the invention into solid tumors results in the selective phagocyte-mediated ablation of the undesirable cells.

The invention provides a method for the treatment of autoimmune disorders in a host, by eliminating autoreactive T-cells. Transformed cells containing a recombinant polynucleotide comprising a promoter operably linked with a polynucleotide coding for an immunostimulatory cell surface polypeptide are administered to a host with an autoimmune disorder. The cells express a therapeutically effective amount of immunostimulatory cell surface polypeptide from the recombinant polypeptide. The immunostimulatory cell surface polypeptide contacting macrophages activates the macrophages to modulate host autoreactive T-cells, thereby reducing the T-cell autoreactivity in the host. Macrophages specifically modulate Th1/Th2 responses. The reactiveness of T-cells differ depending on the availability of co-stimulatory factors. Therefore, T-cells can be induced to become tolerant.

The invention provides a composition in which a transformed cell capable of expressing an immunostimulatory cell surface polypeptide is encapsulated in an immunoisolatory capsule. The transformed cells of the invention are particularly useful when encapsulated for implantation in a human patient, because cells escaping from a ruptured capsule are destroyed by the patient's immune system. A host immune response will not be triggered by the transformed cells expressing an immunostimulatory cell surface polypeptide in an intact device. In case of a device failure, however, the released cells are effectively eliminated by phagocytes without complement activation or the creation of an immune memory.

BRIEF DESCRIPTION OF THE DRAWINGS

FIG. 1A shows the natural configuration of IgG opsonization. FIG. 1B shows a naturally occurring cell surface IgG anchored by type I transmembrane domain, with carboxyl terminus facing cytosol and amino terminus facing out side of cell. FIG. 1C shows a reverse cell surface Fc anchored by type II transmembrane domain, with amino terminus facing cytosol and carboxyl terminus facing out side of cell, mimicking IgG opsonization.

FIG. 3A shows the dose-response effect of anti-serum opsonized BHK cells on superoxide production by mouse macrophages. FIG. 3B shows the effect of BHK-reverse Fc clones on superoxide production by mouse macrophages. The results are presented as $V_{max}$ (nmoles $O_2/10^7$ cells/min), with the numbers in parenthesis representing individual clones.

DETAILED DESCRIPTION OF THE INVENTION

Introduction

Figure 1:
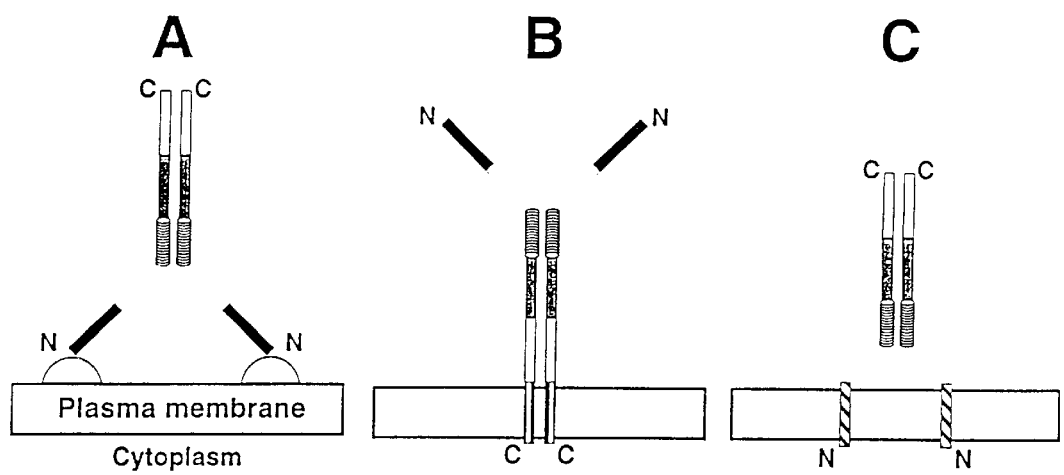
FIG. 1 shows the rationale of the invention in one embodiment.

The invention provides novel recombinant polynucleotides encoding immunostimulatory cell surface polypeptides that, when expressed by a cell, result in rejection of that cell by the host immune system. The invention also provides transformed cells containing the recombinant polynucleotides and methods for using the transformed cells. In specific embodiments described in EXAMPLE 1, a chimeric polypeptide containing the human transferrin receptor membrane domain anchors a human IgG$_1$ Fc to the surface of the cell plasma membrane in a "reversed orientation" (SEQ ID NO:2 and SEQ ID NO:4), thus mimicking the configuration of IgG during opsonization (FIGS. 1A and IC). The human IgG₁ chimeric polypeptide binds the Fc receptor (here, FcγRI) to activate phagocytes, such as macrophages, but avoids the undesirable characteristics of also activating the complement cascade ("complement fixation"). A chronically activated complement system can kill host cells, and accumulating evidence suggests that this mechanism can cause many degenerative diseases, including inflammation and neurodegenerative diseases.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

Immunostimulatory cell surface polypeptide

An "immunostimulatory cell surface polypeptide" is a polypeptide, expressed on a cell surface, that is capable of stimulating an immune response against the cell in a host. As used herein, a "biologically active molecule" is an immunostimulatory cell surface polypeptide. Polypeptides appropriate for use as immunostimulatory cell surface polypeptides include the following:

a. opsonins such as IgG and C3b.

b. proteins with carbohydrate residues that interact with the mannose-fucose receptor of phagocytes;

c. proteins capable of recognition by receptors on scavenger macrophages;

d. ligands for integrins; located on phagocytes;

e. glycoproteins, such as integrins and selectins; and f. fucosyl transferase, which generates a Gal—Gal epitope recognized by macrophages.

The immunostimulatory cell surface polypeptides can be used in either a full-length or a truncated form, as appropriate. In particular, the terms "region" and "domain" as used to describe an immunostimulatory cell surface polypeptide includes either a full-length immunostimulatory cell surface polypeptide or a part of the immunostimulatory cell surface polypeptide, such as the IgG regions and domains described below.

Immunoglobulin G (IgG) is the preferred immunostimulatory cell surface polypeptide for use in this invention. An IgG protein contains (1) an Fab region (including the VH, VL and CH₁ domains); (2) a hinge region, and (3) an Fc region (including the CH₂ and CH₃ domains). The Fab region is the region of an antibody protein which includes the antigen-binding portions. The "hinge" region is a flexible area on the immunoglobulin polypeptide that contains many residues of the amino acid proline and is where the Fc fragment joins one of the two Fab fragments. The Fc region is the constant region on an immunoglobulin polypeptide; is located on the immunoglobulin heavy chains; and is not involved in binding antigens. The Fc region can bind to an Fc receptor on phagocytes. The amino-proximal end of the CH₂ domain, especially amino acids 234 to 237, is important for binding of the Fc region to the Fc receptor. Fc receptors, such as FcγRI, are integral membrane proteins located on phagocytic white blood cells, such as macrophages. The hinge region is important for regulating Fc—Fc receptor interactions, providing flexibility to the polypeptide and functioning as a spacer.

The immunoglobulin polynucleotide used for producing a recombinant immunostimulatory cell surface polypeptide can be from any vertebrate, such as human or mouse (see, EXAMPLE 1). Preferably, the polynucleotide encodes an immunoglobulin having a substantial number of sequences that are of the same origin as the host. For example, if a human is treated with a polypeptide of the invention, preferably the immunoglobulin is of human origin. The immunoglobulin polynucleotide may code for a full length polypeptide or a fragment, such as a fragment of a larger fusion protein, which includes an immunostimulatory cell surface polypeptide and a "second cell surface polypeptide." Some advantages of using an immunoglobulin fusion protein include one or more of (1) possible increased avidity for multivalent ligands, (2) longer serum half-life, (3) the ability to activate effector cells by the Fc domain, and (4) ease of purification (for example, by protein A chromatography). EXAMPLE 1 shows the construction and use of two immunoglobulin fusion proteins.

Figure 2:
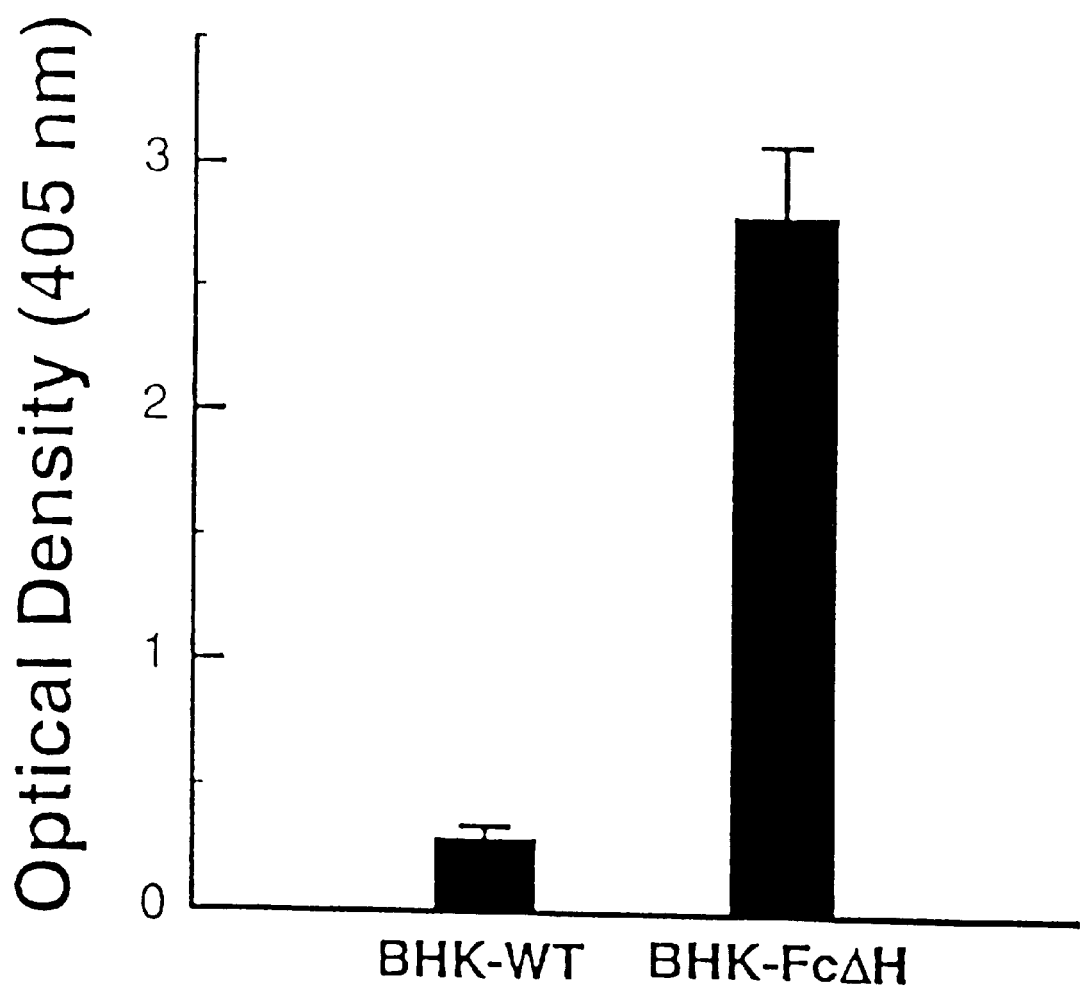
FIG. 2 shows the expression of reverse hTR-FcΔH (SEQ ID NO:4) in BHK cells, with the plasma membrane-associated hIgG determined by an ELISA.

In one embodiment, IgG₁-Fc is expressed on the cell surface in a "reverse orientation" (see, FIG. 2). The Fc is in a reverse orientation (i.e., as a type II protein, with the N-terminus projecting toward the cytosol and the C-terminus projecting away from the cell surface) as compared with the orientation of Fc in the naturally type I cell surface IgG polypeptide (with the C-terminus projecting toward the cytosol and the N-terminus projecting away from the cell surface). In specific embodiments provided in EXAMPLE 1 (SEQ ID NO:2 and SEQ ID NO:4), the reverse orientation results from the fusion of the Fc region with a type II membrane protein transmembrane domain. Cell surface Fc expressed in the reverse orientation, a novel design in this invention, retains the biological function of IgG₁ Fc of binding Fc receptor to mediate macrophage activation, while simultaneously losing the complement fixation capability, as described in EXAMPLE 1.

Only when the CH₁ (e.g., SEQ ID NO:2) or CH₁ and hinge regions (e.g., SEQ ID NO:4) are deleted from IgG₁ is a high level of plasma membrane expression of reverse Fc achieved (see, FIG. 2). Full length IgG₁ heavy chain constant region (hTR-Fc) resides primarily in the endoplasmic reticulum. Removal of the CH₁ domain allows translocation the chimera from the endoplasmic reticulum to the plasma membrane.

Phagocyte activation

Immunostimulatory cell surface polypeptides and their receptors are important for the clearance and destruction of foreign materials, including mammalian cells or bacteria. Immunostimulatory cell surface polypeptides and their receptors activate the phagocytosis and ADCC. The process begins with opsonization of the foreign materials. An opsonin is an agent, usually an antibody or complement components, that makes a cell or microbe more vulnerable to being engulfed by a phagocyte; opsonization is the process of coating a cell with opsonin. A phagocyte is an cell that engulfs and devours another; the process of engulfing and devouring is phagocytosis. Among the important phagocytes for this invention are macrophages and monocytes. Monocytes are a type of large white blood cell that travels in the blood but which can leave the bloodstream and enter tissue to differentiate into macrophages. Macrophages digest debris and foreign cells. Monocytes are generally characterized by the cell surface expression of CD14.

In a specific embodiment of the invention, cells coated with immunoglobulins bind to phagocytes through the Fc receptors on the phagocytes. Phagocytes respond to signals from the Fc receptors by assembling cytoskeletal proteins, signaling cytoskeletal-protein assembly by activation of protein tyrosine kinases, and by phagocytosing the cell coated with immunoglobulin. IgG-FcγRI interaction activates various biological functions such as phagocytosis, endocytosis, ADCC, release of inflammatory mediators and superoxide anion production. Macrophages possess organic anion transporter proteins that promote the afflux of anionic substances from the macrophage. Thus, FcγRI mediates ADCC by macrophages and triggers both phagocytosis and superoxide production. For that reason, the cells and methods of the invention where the Fc domain of IgG is expressed on the surface of the cell to interact with phagocyte Fc receptor cause phagocytes to bind to the cell expressing the Fc domain of IgG, inducing ADCC. The $IgG_1$ and $IgG_3$ isotypes, that interact with the high affinity receptor FcγRI on macrophages, are preferred for the cells and methods of the invention.

Macrophages can also present antigens to T cells. In this way, macrophages are involved in other components of the immune response, including the humoral immune response (antibody production) and cellular immune response.

Absence of complement fixation

A major function associated with human $IgG_1$ is the activation of complement, an undesirable characteristic for encapsulated cell therapy. Activation of complement pathways may lead to a variety of undesirable biologic actions, such as damage cells within a device. The transformed cells of the invention have the useful characteristics of being (1) cells expressing immunostimulatory cell surface polypeptide; (2) so that the immunostimulatory cell surface polypeptide activates macrophages; but (3) the immunostimulatory cell surface polypeptide does not activate the complement cascade.

Figure 5:
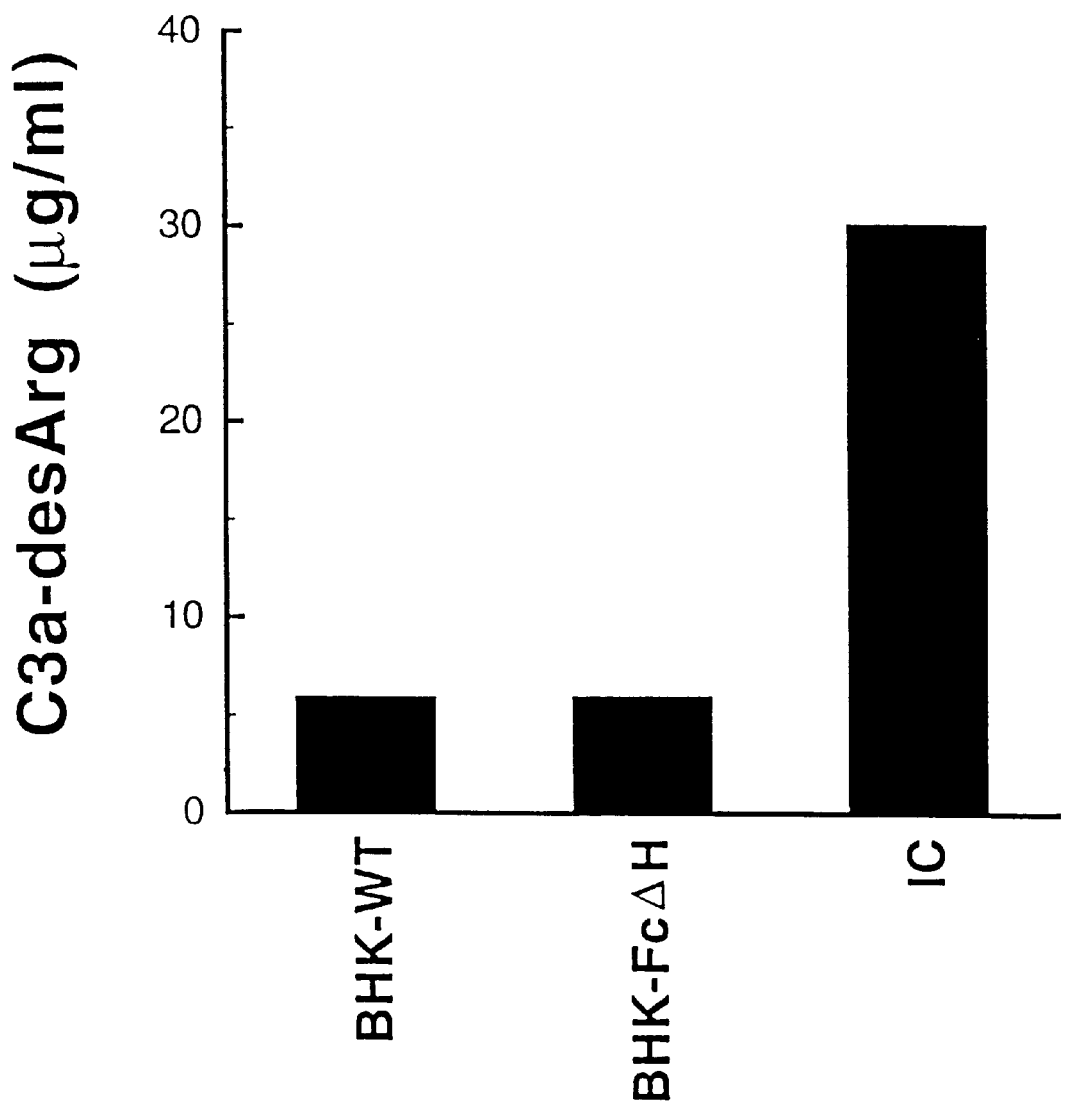
FIG. 5 shows the effect of BHK-FcΔH induced (SEQ ID NO:4) in complement activation. C3a-desArg enzyme immunoassay was performed following pretreatment of human serum with BHK-WT, BHK-FcΔH induced (SEQ ID NO:4) and immune complexes (IC).

In EXAMPLE 1, in an embodiment where the immunostimulatory cell surface polypeptide is a Fc in a reversed orientation, a C3a enzyme immunoassay showed that no complement fixation occurs (FIG. 5). By contrast, immune complexes containing intact IgG activated complement effectively. This is consistent with observations that $IgG_1$ heavy chain $CH_1$ and hinge domains are important for complement activation. Thus, although a high level of Fc is expressed on the cell surface, the chimera of $IgG_1$ heavy chain with $CH_1$ and hinge deletion (e.g., SEQ ID NO:4) do not activate complement, despite being a potent stimulus for macrophages.

Immunostimulatory cell surface polypeptide fused to a second cell surface polyveptide In one embodiment, the immunostimulatory cell surface polypeptide is fused to a second cell surface polypeptide to form a single polypeptide expressed at the cell surface. The second cell surface protein anchors the immunostimulatory cell surface polypeptide to the exterior of the cell. Examples of second cell surface proteins that may be suitable for such use include transferrin, CD10, CD13, CD23, CD26, CD38, CD71, CD72, CD74, 4F2, BP-1, endoglin, Ly-49, M-ASGP-BP, NKG2A, NKR-PI, and PC-1. Of these cell surface molecules, CD71, CD72, BP-1, endoglin, Ly-49, NKR-PI and PC-1 are preferred because these polypeptides are known to dimerize and can facilitate dimerization of the Fc region of the antibody, for the enhanced stability of Fc.

The second cell surface polypeptide can be human transferrin receptor (hTR), a type II cell surface protein. In a specific embodiment, the extracellular region of the transferrin receptor substitutes for the native hinge region of IgG to anchor Fc (residues 89–97). The hTR fragment is approximately equal in length, but not in amino acid identity, to native $IgG_1$ hinge, and may effectively provide spacer functions similar to that of the hinge region. Also, the hinge region of IgG provides intermolecular disulfide bonds between heavy and light chains using critical cysteine residues. The hTR region (1-97) contains at least one cysteine (C89) to mimic the hinge region function, by allowing multimeric association of the hTR-FcΔH monomers.

Transformed cells and recombinant genetic techniques

A "transformed" cell is a cell or progeny of a cell into which has been introduced, by means of recombinant genetic techniques, a polynucleotide encoding a cell surface protein. The term "recombinant" refers to a product of human intervention. The transformed cell may be any human cell that can express an immunostimulatory cell surface polypeptide. Any suitable source of human tissue, can be used as a source for generating transformed cells, including publicly available immortalized cell lines and dividing primary cell cultures. Examples of human cell lines include human neural stem or progenitor cells; RPMI 2650, HT-1080 or SW-13 epithelial cells; HL-60 macrophage cells; CCRF-CEM or RPMI 8226 lymphoid cells; and WI-38, HEL1, MRC-5 or IMR-90 fibroblast cells. Useful human cell lines have the ability to be easily transfected, and to secrete proteins and peptides.

Figure 3:
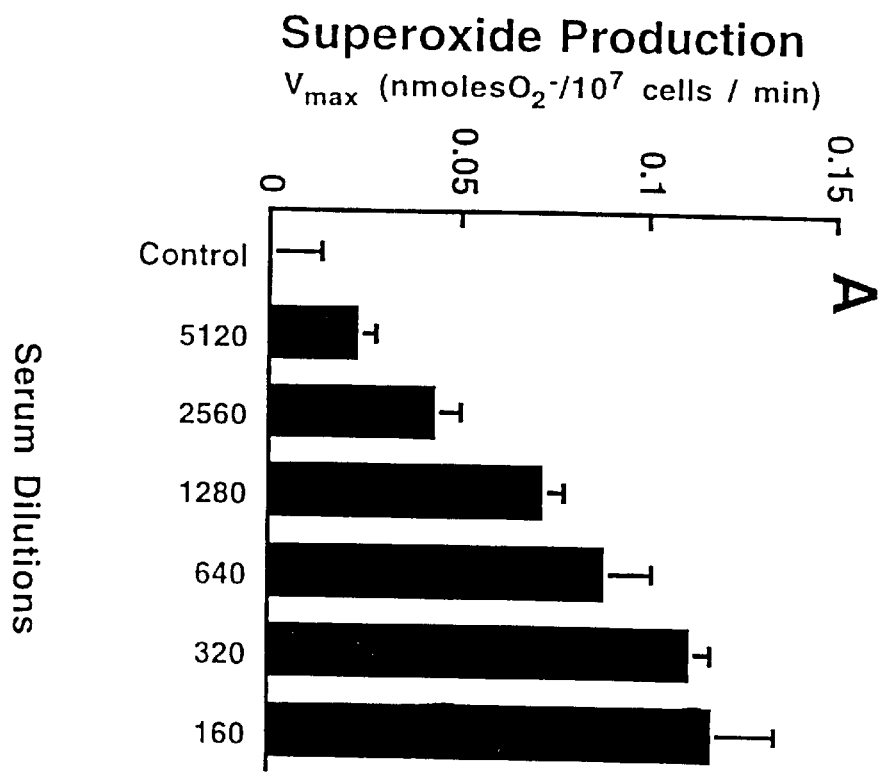
FIG. 3 shows the effect of cell surface IgG Fc, either intact IgG or recombinant reverse Fc, on superoxide production.
Figure 3:
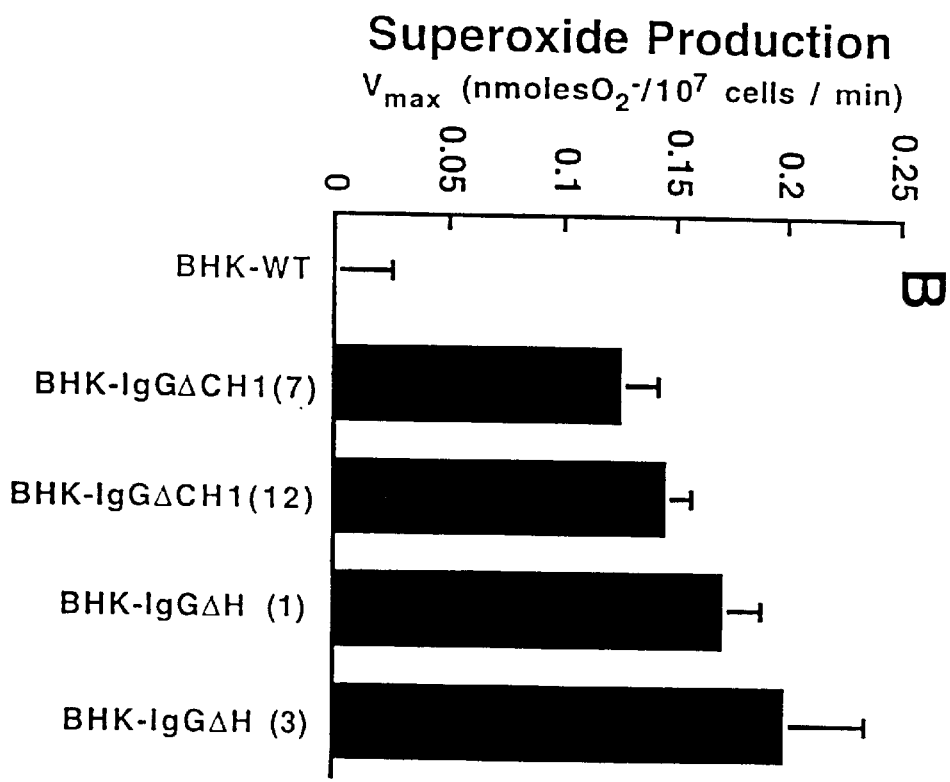

The transformed cells can be from other mammalian sources, for example, from rodents. In EXAMPLE 1, baby hamster kidney (BHK) cells opsonized with different concentrations of antibody stimulated a dose-dependent increase in superoxide production (FIG. 3A). Similarly, transformed BHK-Fc cells induce superoxide production. Thus, the presence of IgG Fc on the cell surface of transformed hamster cells activate macrophages.

A recombinant polynucleotide encoding an immunostimulatory cell surface polynucleotide can be constructed in a standard DNA expression vector and introduced to a cell for expression within the cell. Polynucleotides for insertion into cloning vectors, for example coding polynucleotides, can be constructed using the polymerase chain reaction (PCR) to amplify appropriate polynucleotides. Polynucleotide synthesis and purification techniques are described in Sambrook et al. (*Molecular Cloning: A Laboratory Manual*, Cold Spring Harbor Laboratory Press, 1989) and *Current Protocols in Molecular Biology* (Ausubel et al., Eds., Wiley Interscience, N.Y. 1993). The PCR procedure is performed by well-known methodology. See, for example, Ausubel et al, and Bangham (In *Protocols in Molecular Genetics*, Humana Press, 1991). Moreover, PCR kits can be purchased from companies such as Stratagene Cloning Systems (La Jolla, Calif.) and Invitrogen (San Diego, Calif.). The products of PCR are subdloned into cloning vectors. The use of PCR for bacterial host cells is described, for example, by Hofmann et al. (In *PCR Protocols and Applications*, White, Ed., Humana Press, 1993, pp. 205–210), and by Cooper et al. (Id. at pp. 305–316). Coding polynucleotides are constructed by PCR in EXAMPLE 1.

A "vector" is a replicon to which coding polynucleotide is attached, so as to bring about the replication or expression of the attached coding polynucleotide. Vectors can be used for the transformation of cells in gene manipulation bearing a coding polynucleotide corresponding to appropriate polypeptides that, when combined with appropriate control sequences, confer specific properties on the transformed cell. Recombinant vectors are constructed by cutting and joining polynucleotides from different sources using restriction enzymes and ligases.

Vectors include cloning vectors and expression vectors. A cloning vector is a polynucleotide, such as a plasmid, cosmid or bacteriophage, that can replicate autonomously in a host prokaryotic or eukaryotic cell. Cloning vectors typically contain one or a small number of restriction endonuclease recognition sites at which polynucleotide sequences can be inserted in a determinable fashion without loss of an essential biological function of the vector, as well as a marker gene that is suitable for use in the identification and selection of cells transformed with the cloning vector. Suitable cloning vectors are described by Sambrook et al. (*Molecular Cloning: A Laboratory Manual*, Cold Spring Harbor Laboratory Press, 1989); *Current Protocols in Molecular Biology* (Ausubel et al., Eds., Wiley Interscience, N.Y. 1993), and *Molecular Biology LabFax* (Brown, Ed., Academic Press, 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

Cloned variants are amplified by transforming competent bacterial cells with a cloning vector and growing the bacterial host cells in the presence of the appropriate antibiotic (see, for example, Sambrook et al., and Ausubel et al., above). Bacterial host cells are then screened for the appropriate clones.

The resulting recombinant polynucleotide or relevant parts can be cloned from cloning vectors into expression vectors, which expression vectors have characteristics permitting higher levels of, or more efficient expression of, the resident polynucleotides. These constructs may require a promoter that initiates transcription of the inserted coding polynucleotide. A "promoter" is a polynucleotide sufficient to direct transcription, including those promoter elements which are sufficient to render promoter-dependent gene expression inducible. Typically, a polynucleotide encoding a biologically active cell surface protein polypeptide is operably linked to a promoter. "Operably linked" refers to a juxtaposition where the components are configured so as to perform their usual function. Thus, promoter operably linked to a coding polynucleotide is capable of effecting the expression of the coding polynucleotide. By "operably linked" is meant that a coding polypeptide and a promoter are functionally connected to permit gene expression when the appropriate factors (e.g., transcriptional activator proteins) are bound to the regulatory sequence. The orientation or placement of the elements of the vector is not strict, so long as the operable linkage requirement is fulfilled for control of and expression of the coding polynucleotide. A "mammalian" promoter is a polynucleotide that directs transcription in a mammalian cell (e.g., a promoter of a mammal or a virus that infects a mammal). Transcriptional regulatory sequences include a promoter region sufficient to direct the initiation of RNA synthesis. Suitable eukaryotic promoters include the promoter of the mouse metallothionein I gene (Hamer et al., *J Molec. Appl. Genet.* 1: 273, 1982); the TK promoter of Herpes virus (McKnight, Cell 31: 355, 1982); the SV40 early promoter (Benoist et al., *Nature* 290: 304, 1981); the Rous sarcoma virus promoter (Gorman et al., *Proc. Nat'l Acad. Sci. USA* 79: 6777 1982); and the cytomegalovirus promoter (Foecking et al., *Gene* 45: 101, 1980).

Many genetic constructs and methods for expressing heterologous genes in cells of mammals are known in the art and are suitable for use in the invention. For example, expression of a cell surface protein can be accomplished with conventional gene therapy methods, such as those that employ viral vectors (e.g., vectors derived from retroviruses, adenoviruses, herpes viruses, vaccinia viruses, polio viruses, sindbis viruses, or adeno-associated viruses).

Constitutive expression

In one embodiment, the immunostimulatory cell surface polypeptide is constitutively expressed in the transformed cell. Constitutive expression is achieved by the use of a vector with a constitutive promoter. For example, the vector pRc/CMV (Invitrogen, San Diego, Calif.) provides a high level of constitutive transcription from mammalian enhancer-promoter sequences. Another constitutive promoter is the interferon-inducibleMx-1 promoter. The level of expression may depend on the immunostimulatory cell surface polypeptide used, on the vector copy number, or the vector cellular or genomic location, by does not, by contrast with inducible expression, depend on the addition of factors.

Constitutive expression can occur when the recombinant polynucleotide becomes part of the genome of an organism (i.e., either stably integrated or as a stable extrachromosomal element) that develops from that cell. Such a polynucleotide may include a gene which is partly or entirely heterologous (i.e., foreign) to the transgenic organism, or may represent a gene homologous to an endogenous gene of the organism.

Increased constitutive or inducible expression can be achieved by increasing or amplifying the vector copy number using amplification methods well known in the art. Such amplification methods include, e.g., DHFR amplification (see, e.g., Kaufinan et al., U.S. Pat. No. 4,470,461) or glutamine synthetase ("GS") amplification (see, e.g., U.S. Pat. No. 5,122,464, and European Patent Application Publication No. EP 338,841). Expression vectors containing the geneticin (G418) or hygromycin drug selection genes (Southern, In Vitro, 18: 315, 1981, Southern & Berg, *J Mol. Appl. Genet.*, 1: 327, 1982) are also useful. These vectors can employ a variety of different enhancer/promoter regions to drive the expression of both a biologic gene of interest and a gene conferring resistance to selection with toxin such as G418 or hygromycin B. The G418 resistance gene codes for aminoglycoside phosphotransferase (APH) which enzymatically inactivates G418 added to the culture medium. Only those cells expressing the APH gene will survive drug selection usually resulting in the expression of the second biologic gene as well. The hygromycin B phosphotransferase (HBH) gene codes for an enzyme that specifically modifies hygromycin toxin and inactivates it. Genes co-transfected with or contained on the same plasmid as the hygromycin B phosphotransferase gene will be preferentially expressed in the presence of hygromycin B.

Inducible expression

In another embodiment, the expression vector encoding the immunostimulatory cell surface polypeptide is inducible. High levels of expression can be accomplished by the addition of a regulatory region which provides increased transcription of downstream sequences in the appropriate host cell. For a mammalian host, the transcriptional and translational regulatory signals preferably are derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

The invention therefore provides a "suicide gene" for use in therapy. In this embodiment, transformed cells are used to provide a pharmacologically effective treatment. When treatment is no longer desirable (for any reason, such as the treatment being unsuccessful or the treatment being successfully completed), expression of the immunostimulatory cell surface polypeptide is induced. The expression results in the transformed cell being effectively removed from the patient.

Expression in the central nervous system

The brain is an immunologically privileged site, sheltered from circulating cells and proteins of the immune system; but a growing body of evidence implicates complement in numerous brain diseases (see review by Morgan et al., *Immunopharmacology* 38(1–2):43–50, 1997). Complement synthesis and activation in the brain are important in immune defense at this site, but may also be of importance in CNS conditions such as Alzheimer's disease, ischaemia and Parkinson's disease, as well as in peripheral disorders such as myocardial ischaemia and xenotransplantation (McGeer & McGeer, *Drugs*55(6):739–46, 1998). In Alzheimer disease (AD) cases, positive staining for classical pathway complement proteins C1q, C1r, C1s, C2, C3, C4, C5, C6, C7, C8 and C9 was observed in pyramidal neurons and senile plaques (Terai et al., *Brain Res* 769(2):385-90, 1997; Shen et al, *Brain Res* 769(2):391-5, 1997). Some brain cells synthesize complement and also express specific receptors; some are exquisitely sensitive to the lytic effects of complement. Complement activation causes neuronal cell death in vitro, and this neurodegenerative process is regulated by homologous restriction, as described by Shen et al. (*Brain Res Brain Res Protoc* 1(2):186–94, 1997). Thus, the cells, compositions, and methods of the invention are useful in modulation of the central nervous system immune response.

In one embodiment, the promoter can be cell-specific, tissue-specific, or stage-specific, to express the immunostimulatory cell surface polypeptide in neural cells with increased specificity. Examples of expression vectors that can be employed are the commercially available pRC/CMV, pRC/RSV, and pCDNAINEO (Invitrogen), where the viral promoter regions of interest are replaced with promoter sequences that are not subject to the down regulation experienced by viral promoters within the central nervous system. For example, the GFAP promoter can be employed for the transfection of astrocytes and the MBP promoter can be used in oligodendrocytes. Other promoters include, but are not limited to, the promoters of hDBH (human dopamine beta hydroxylase) (Mercer et al., *Neuron* 7: 703–716, 1991)), hTH (human tyrosine hydroxylase) (Kaneda et al, *Neuron* 6: 583–594, 1991), hPNMT (human phenylethanolamine N-methyltransferase) (Baetge et al., *PNAS*, 85: 3648–3652, 1988), mGFAP (mouse glial fibrillary acidic protein) (Besnard et al., *J Biol. Chem.*, 266: 18877–18883, 1991)), myelin basic protein (MBP), mNF-L (mouse neurofilament-light subunit) (Nakahira et al., *J Biol. Chem.*, 265: 19786–19791, 1990), hPo (human $P_o$, the promoter for the gene encoding the major myelin glycoprotein in the peripheral nervous system) (Lemke et al., *Neuron*, 1: 73–83, 1988), mMT, rNSE (rat neuron-specific enolase) (Sakimura, et al, *Gene* 60: 103–113, 1987), and the like.

Diagnostic methods

The transformed cells or immunostimulatory cell surface polypeptides of the invention are diagnostically useful for the detection of macrophage response to immunostimulatory cell surface polypeptides, for example, in inflammation. Biological samples, e.g. blood or derivatives thereof, biopsies, synovial fluid, etc., can be assayed. Assays may be performed on cell lysates, intact cells, frozen sections, etc. Many clinically significant disorders are accompanied by inflammation, e.g. arthritis, bacterial infections, hypersensitivity, wound healing, etc. In a representative screening assay, the activation of in vitro phagocytes, such as macrophages, by in vitro cells expressing immunostimulatory cell surface polypeptides is measured, as an in vitro test of a patient's macrophage ability to ingest and kill specific target cells. Alternatively, purified or semi-purified immunostimulatory cell surface polypeptide may be bound to an insoluble substrate, and used in lieu of the cells or tissue.

The immunostimulatory cell surface polypeptides are also diagnostically useful in screening assays to determine whether an agent is effective in interfering with the interaction between phagocytes and immunostimulatory cell surface polypeptides. In a representative screening assay, the activation of in vitro phagocytes, such as macrophages, by in vitro cells expressing immunostimulatory cell surface polypeptides is measured. Agents, particularly peptides, aptamers, carbohydrates, small organic molecules, etc. are added to the mixture of antibody and cells, and a measured reduction in phagocyte activity indicates that the compound reacts with the immunostimulatory cell surface polypeptide.

The term "agent" describes any molecule, e.g. protein or pharmaceutical, with the capability of altering or mimicking the physiological function of a phagocyte. Generally a plurality of assay mixtures are run in parallel with different agent concentrations to obtain a differential response to the various concentrations. Typically, one of these concentrations serves as a negative control, i.e. at zero concentration or below the level of detection.

Also included in the screening method of the invention are combinatorial chemistry methods for identifying chemical compounds. See, for example, Plunkett & Ellman, ("Combinatorial Chemistry and New Drugs." *Scientific American*, April, 69, 1997). Areas of investigation for combinatorial chemistry are the development of therapeutic treatments. Drug screening identifies agents that provide a replacement, enhancement or regulation of function in affected cells. Of particular interest are screening assays for agents that have a low toxicity for human cells.

Candidate agents encompass numerous chemical classes, though typically they are organic molecules, preferably small organic compounds having a molecular weight of more than 50 and less than about 2,500 daltons (Da). Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification or amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein—protein binding and/or reduce non-specific or background interactions. Reagents that improve the efficiency of the assay, such as protease inhibitors, nuclease inhibitors or anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Second antigen presentation

The invention provides a method for antigen presentation. Mildly or minimally antigenic substances ("second antigens") are introduced to the immune system. In one embodiment, the second antigens are on the surface of a transformed cell containing a recombinant polynucleotide with a promoter operably linked to a polynucleotide coding for an immunostimulatory cell surface polypeptide. In another embodiment, the transformed cell containing a recombinant polynucleotide with a promoter operably linked to a polynucleotide coding for an immunostimulatory cell surface polypeptide actually makes the second antigenic substances. For example, the second antigen could be encoded by a recombinant polynucleotide that has been used to transform the cell. In other words, transformed cells can be constructed by recombinant techniques to express the second antigen against which a strong immune response is desired. This method of the invention is useful for promoting a significant immune response against otherwise weak antigens. Among the weak antigens are tumor associated antigens or certain viral antigens, e.g., specific antigens of HIV-1, etc.

Method for stimulating phaeocyte activity

The invention provides a method for stimulating phagocyte activity. A transformed cell containing a recombinant polynucleotide with a promoter operably linked to a polynucleotide coding for an immunostimulatory cell surface polypeptide is made to contact a phagocyte, such as a macrophage. The contact stimulates an increased phagocytic activity by the phagocyte. The phagocyte may engulf the transformed cell. The phagocyte may also or alternatively engulf other cells, or exhibit measurable properties of activated macrophages, such as those described in EXAMPLE 1.

This method is useful for targeting a therapeutic compound to a macrophagic tumor. A therapeutic compound, for example an anti-tumor compound, is introduced into a transformed cell containing a recombinant polynucleotide with a promoter operably linked to a polynucleotide coding for an immunostimulatory cell surface polypeptide. This transformed cell is introduced into a host, such as a patient. The transformed cell is targeted to the macrophagic tumor, which phagocytoses the transformed cell. Thus, the therapeutic compound is delivered.

Modulating an immune response

The invention also provides a method for modulating an immune response using transformed cells expressing immunostimulatory cell surface polypeptides. The term "modulate" means that the phagocyte activity is controlled or regulated in vivo by the methods of the present invention. The term "modulate" can mean either stimulating or inhibiting the response, depending on the situation. The method of the invention includes treatment of conditions in which either the immune reactions are deleterious and suppression of such responses or immune reactions is desirable, or conditions in which immune reactions are important and stimulation of such responses is desirable. An immunostimulatory cell surface polypeptide may be useful in recruiting or activating macrophages that would enhance the immune response to a vaccine, stimulate a response for tumor rejection, or alter the response in a qualitative manner. Similarly, the immunostimulatory cell surface polypeptide may inhibit or depress an immune or inflammatory response where desirable, such as in graft rejection responses after organ and tissue transplantations, or autoimmune disease. Some of the commonly performed transplantation surgeries include organs and tissues such as kidneys, hearts, livers, skin, pancreatic islets and bone marrow.

Autoimmune disorders

"Autoimmune disorders" include the group of diseases caused by reactions of the immune system to self antigens leading to tissue destruction. The immune system's response may be primarily humoral (autoantibody production), primarily cellular (delayed-type hypersensitivity T-cells and perhaps cytotoxic T-cells, i.e., "autoreactive T cells"), or, both humoral and cellular reactions may be induced. The highly specific reactivity of autoreactive T-cells is directed against external cell-surface structures, internal cytoplasmic or nuclear constituents, or against secreted products produced by cells in different organs. There is clearly a problem of some kind regarding the development of self-antigen reactive $T_H$-cells. In the method of the invention, expression of an immunostimulatory cell surface polypeptide results on the elimination of autoreactive t-cells, thus reducing a factor involved in the autoimmune disorder.

Some important autoimmune diseases include diabetes; autoimmune thyroiditis; multiple sclerosis and related demyelinating diseases; rheumatoid arthritis; systemic lupus erythematosis; and myasthenia gravis. Other autoimmune and related disorders include, e.g., polyarteritis nodosa: polymyositis and dermatomyositis: progressive systemic sclerosis (diffuse scleroderma): glomerulonephritis: Sjogren's syndrome: Hashimoto's disease and Graves' disease: adrenalitis: hypoparathyroidism: pernicious anemia; uveitis pemphigus and pemphigoid; cirrhosis and other diseases of the liver; ulcerative coliris; myocarditis; regional enteritis; adult respiratory distress syndrome; local manifestations of drug reactions (dermatitis, etc.); inflammation-associated or allergic reaction patterns of the skin; atopic dermatitis and infantile eczema; contact dermatitis, psoriasis lichen planus; allergic enteropathies; atopic diseases, e.g. allergic rhinitis and bronchial asthma; transplant rejection (heart, kidney, lung, liver, pancreatic islet cell, others); hypersensitivity or destructive responses to infectious agents; poststreptococcal diseases e.g. cardiac manifestations of rheumatic fever, etc.

Encapsulation

The invention provides a composition in which transformed cells containing polynucleotides encoding an immunostimulatory cell surface polypeptide is encapsulated in an immunoisolatory capsule. An "immunoisolatory capsule" means that the capsule upon implantation into a host minimizes the deleterious effects of the host's immune system on the cells within the core. In the rare event that encapsulated cells should escape from a capsule whose integrity has been breached, the cells can be immediately eliminated by the host without triggering specific immunological memory. When encapsulated, the transformed cell does not activate macrophages, but unencapsulated cells are effectively eliminated by the host.

Encapsulated cell therapy is a valuable therapeutic method. Encapsulated cell therapy is based on the concept of isolating cells from a host's immune system by surrounding the cells with a semipermeable biocompatible material before implantation within the host. Using encapsulation techniques, cells can be transplanted into a host without immune rejection or use of immunosuppressive drugs. Useful biocompatible polymer capsules usually contain (a) a core which contains a cell or cells, either suspended in a liquid medium or immobilized within an immobilizing matrix, and (b) a surrounding or peripheral region of permselective matrix or membrane ("jacket") which does not contain isolated cells, which is biocompatible, and which is sufficient to protect isolated cells if present in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue. This technique prevents the inherent risk of tumor formation and allows the use of the transformed cells without immunosuppression of the recipient. Moreover, the implant may be retrieved if necessary or desired.

The capsule is made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, nutrients, while metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by Aebischer et al. (International Patent Application No. WO 92/19195); Baetge (International Patent Application Publication No. WO 95/05452); or U.S. Pat. Nos. 5,639,275; 5,653,975; 4,892,538; 5,156,844; 5,283,187; and 5,550,050. Such capsules will allow for the passage of metabolites, nutrients and therapeutic substances while minimizing the detrimental effects of the host immune system. Components of the biocompatible material may include a surrounding semipermeable membrane and the internal cell-supporting scaffolding. preferably, the transformed cells are seeded onto the scaffolding, which is encapsulated by the pemiselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fiber structures can be used for cell implantation (U.S. Pat. No. 5,512,600). Further, biodegradable polymers can be use as scaffolds for hepatocytes and pancreatic cells. as reviewed by Cima et al. (*Biotech. Bioeng.* 38: 145–58, 1991). Biodegradable polymers include those comprised of poly(lactic acid) PLA, poly(lactic-coglycolic acid) PLGA, and poly (glycolic acid) PGA and their equivalents. Foam scaffolds have been used to provide surfaces onto which transplanted cells may adhere. Woven mesh tubes have been used as vascular grafts. Additionally, the core can be composed of an immobilizing matrix formed from a hydrogel, which stabilizes the position of the cells. A hydrogel is a three dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly (acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by Aebischer & Wahlberg (U.S. Pat. No. 5,284,761; U.S. Pat. No. 5,158,881). The surrounding semipermeable membrane is formed from a polyether sulfone hollow fiber, such as those described by Wechs (U.S. Pat. No. 4,976,859) and Muller & Wechs (U.S. Pat. No. 4,968,733). An alternate surrounding semipermeable membrane material is poly(acrylonitrile/covinly chloride).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient's blood vessels, are not preferred. Certain shapes, such as rectangles, patches, disks, cylinders, and flat sheets offer greater structural integrity and are preferable where retrieval is desired.

When macrocapsules are used, preferably between $10^3$ and $10^8$ cells are encapsulated, most preferably $10^5$ to $10^7$ cells are encapsulated in each device. Dosage may be controlled by implanting a fewer or greater number of capsules, preferably between 1 and 10 capsules per patient.

The scaffolding may be coated with extracellular matrix (ECM) molecules. Suitable examples of ECM molecules include, for example, collagen, laminin, and fibronectin. The surface of the scaffolding may also be modified by treating with plasma irradiation to impart charge to enhance adhesion of cells.

Any suitable method of sealing the capsules may be used, including the employment of polymer adhesives and/or crimping, knotting and heat sealing. In addition, any suitable "dry" sealing method can also be used, as described, e.g., in U.S. Pat. No. 5,653,687.

Many implantation sites are contemplated for the devices and methods of this invention. These implantation sites include the central nervous system, including the brain, spinal cord, and aqueous and vitreous humors of the eye.

The following examples are presented in order to more fully illustrate the preferred embodiments of the invention. These examples should in no way be construed as limiting the scope of the invention, as defined by the appended claims.

EXAMPLE 1

CLONING AND EXPRESSION OF IgG$_1$ cDNA IN REVERSE ORIENTATION

In this EXAMPLE, IgG$_1$ Fc chimera, with the Fc in a reversed orientation, were constructed and successfully expressed on a cell surface. The Fc receptor binding property was retained in the molecules, while the complement activation capability was absent.

Rationale of the design and construction of chimeric hTR-hIgG$_1$ expression cassette and chimeric hTR-mIgG$_1$ expression cassette The rationale of this EXAMPLE was to genetically modify cells to express IgG Fc in a reversed orientation on the cell surface, mimicking natural IgG opsonization for cell elimination. The concept is presented in FIG. 1. In the case of IgG opsonization, IgG binds to the target through Fab portion of the molecule, exposing the Fc portion for Fc receptor binding (FIG. 1A). To express Fc in a similar configuration, the Fc molecule must be anchored to the plasma membrane in a reverse orientation with respect to naturally occurring membrane bound IgG (FIG. 1B). Such a reversed Fc must be anchored by the N-terminus with the carboxyl terminus projecting away from the cell surface (FIG. 1C), in contrast to the naturally occurring membrane bound IgG, which is anchored to the membrane via the Fc portion (FIG. 1B). A type II transmembrane domain is necessary to achieve such a configuration. The hTR is a type II transmembrane protein with the transmembrane region also functioning as a signal peptide. The transmembrane domain of the human transferrin receptor was fused in-frame to the N-terminus of the second and third domains of human immunoglobulin G1 heavy chain constant region. This fusion molecule was designed to take advantage of the type II membrane anchor property of the transferrin receptor to express the Fc portion of the molecule in a reverse orientation, such that the Fc portion projected away from the cell surface. This is in contrast to the conventional cell surface $IgG_1$ which is anchored by a C-terminal type I transmembrane domain.

Taking advantage of such a property, a chimeric protein containing the hTR transmembrane domain and human IgG Fc domain was designed. The cell surface expressed reverse Fc no longer activated complement but retained Fc receptor binding capability, and activated superoxide production by macrophages. This activity was completely blocked by a FcγRI-specific monoclonal antibody.

Primers

To facilitate the cloning of $IgG_1$ RT-PCR products into the pcDNA3.1(−) expression vector, synthetic restriction enzyme sites were engineered at the 5' ends of the above oligonucleotides. Specifically, BamHI and EcoRI sites were engineered in oligonucleotides #400 (SEQ ID NO:5) and #404, respectively, as underlined below. Oligonucleotides #401 (SEQ ID NO:6) and #405 contain the synthetic HindIII restriction sites at the 5' end, as double-underlined below.

For human $IgG_1$ RT-PCR, oligonucleotides #400 (SEQ ID NO:5) and #401 (SEQ ID NO:6) were used:

400: 5'-CCC GGA TCC GCC TCC ACC AAG GGC CCA TGC GTC-3'

401: 5'-CCC AAG CTT CAT TTA CCC GGA GAC AGG GAG AGG-3'

To generate the chimeric human transferrin receptor-human $IgG_1$ ("hTR-$hIgG_1$") fusion expression cassette, oligonucleotides #402 (SEQ ID NO:7) and #403 (SEQ ID NO:8) were used. Oligonucleotide #402 (SEQ ID NO:7) is specific for the human transferrin receptor and contains the synthetic BamHI restriction site, as single underlined below:

402: 5'-CCC GGA TCC GCC ACC ATG.ATG GAT CAA GCT AG-3'

Oligonucleotide #403 (SEQ ID NO:8) is specific for the human transferrin receptor (GAC CGA TGG GCC CTT GGT GGA GGC) and the human $IgG_1$ (CTC AGT TTT TGG).

403: 5'-GAC CGA TGG GCC CTT GGT GGA GGC CTC AGT TTT TGG-3'

For the mouse $IgG_1$ RT-PCR, oligonucleotides #404 (SEQ ID NO:9) and #405 (SEQ ID NO:10) were used):

404: 5'-CCC GAA TTC GCC AAA ACG ACA CCC CCA TCT G-3'

405: 5'-CCC AAG CTT CAT TTA CCA GGA GAG TGG GAG AG-3'

To generate the chimeric human transferrin receptor-mouse $IgG_1$ ("hTR-$mIgG_1$") fusion expression cassette, oligonucleotides #406 (SEQ ID NO:11), #407 (SEQ ID NO:12), #408 (SEQ ID NO:13), and #409 (SEQ ID NO:14) were used. Oligonucleotides #407 (SEQ ID NO:12) and #408 (SEQ ID NO:13) are complementary to each other:

407: 5'-TGT CCT TTT GGC CTC AGT TTT TGG TTC TAC-3'

408: 5'-CCA AAA ACT GAG GCC AAA ACG ACA CCC CCA-3'

Oligonucleotide #408 has the 5' 12 nucleotides identical to the hTR sequence and the 3' 18 nucleotides identical to the $mIgG_1$ sequence. Oligonucleotide #407 (SEQ ID NO:12) has the 5' 12 nucleotides identical to the $mIgG_1$ sequence and the 3' 18 nucleotides identical to the hTR sequence.

Oligonucleotides #406 (SEQ ID NO:11) and #409 (SEQ ID NO:14) are specific for the hTR and $MIgG_1$ sequences, respectively. As underlined below, oligonucleotide #406 (SEQ ID NO:11) contains a synthetic EcoRI site at the 5' end, while oligonucleotide #409 (SEQ ID NO:14) contains an internal BamHI restriction site.

406: 5'-CCC GAA TTC GCC ACC ATG ATG GAT CAA GCT AG-3'

409: 5'-GTG TGC ACA CCG CTG GAC AGG GAT CCA GAG-3'

PCR reactions

N-terminal deletions of the Fc portion of human $IgG_1$, lacking the Fab, $CH_1$ or the hinge domains, were created by the polymerase chain reaction (PCR) and fused in frame to the transmembrane domain of the human transferrin receptor (hTR). Residues 1–97 of hTR, which includes the putative signal sequence and transmembrane domain, and human $IgG_1$ N-terminal deletion fragments were amplified from human spleen cDNA (Clontech, San Diego, Calif.) by PCR using the Advantage GC Genomic PCR kit (Clontech, San Diego, Calif.). The $IgG_1$ region encoding the $CH_1$, hinge, $CH_2$, and $CH_3$ domains was generated by RT-PCR of the human and mouse spleen total RNA. Total RNA was extracted from human or mouse cells by the acid/phenol method described by Chomczynski & Sacchi (*Anal. Biochem.*, 162: 156–159, 1987). RT-PCR was performed as previously described by Gandelman et al (*J Neurochem.*, 56: 1024–1029, 1990). The source of the human transferrin receptor ("hTR") was the plasmid HBMAC38 (ATCC 100808) from the American Type Culture Collection ("ATCC") in Rockville, Md.

Briefly, 0.5 µg of total RNA was reverse transcribed to generate cDNA in a 20 ml reaction mixture according to Krug & Berger (*Methods Enzymol.*, 152: 316–325, 1987). One to 5 µl of each reaction mixture was added to make a final 50 µl PCR mixture containing 10 pmol each of oligonucleotides #400 (SEQ ID NO:5) and #401 (SEQ ID NO:6) for the human $IgG_1$ RT-PCR, and #404 (SEQ ID NO:9) and #405 (SEQ ID NO:10) for the mouse $IgG_1$ RT-PCR. One hundred ng of template DNA HBMAC38 was added to a 50 µl PCR reaction mixture containing 10 mM Tris-HCl (pH 8.3), 50 mM KCl, 800 nM of each of four dNTP, 2 mM $MgCl_2$, 400 nM each of oligonucleotides #402 and #403, and 2.5 units of Taq DNA polymerase (Boehringer Mannheim, Germany). PCR reactions were also carried out using oligonucleotide pairs #406 (SEQ ID NO:11) and #407 (SEQ ID NO:12); and oligonucleotide pairs #408 (SEQ ID NO:13) and #409 (SEQ ID NO:14); on templates HBMAC38 and pcDNA3.1(−)-mIgG$_1$ plasmids, respectively. Reaction mixtures were subjected to 30 cycles of PCR. Each cycle consisted of denaturation at 94° C. for 1 minute, annealing at 50° C. for 1 minute, and extension at 72° C. for 1 minute. The PCR fragment was purified away from the used deoxynucleotides and salt in PCR reaction mixtures by the QIAquick solution purification kit (Qiagen, Chatsworth, Calif.) according to the manufacturer's protocol.

The purified human and mouse $IgG_1$ RT-PCR fragments were digested by BamHI/HindIII and EcoRV/HindIII, respectively, and subsequently ligated into pcDNA3.1(−)/BamHI/HindIII and pcDNA3.1(−)/EcoRI/HindIII, respectively, which was dephosphorylated by alkaline phosphatase treatment. The hTR and IgG heavy chain fragments were ligated, generating the coding sequence for the chimeric molecule. These chimeras were designated hTR-Fc (containing $IgG_1$ heavy chain constant region, full length), hTR-FcΔCH$_1$ (CH$_1$ domain deleted IgG$_1$ heavy chain constant region; SEQ ID NO:1) and hTR-FcΔH (CH$_1$ and hinge deleted IgG$_1$ heavy chain constant region; SEQ ID NO:3) respectively. The ligation mixtures were transformed into DH5a, and ampicillin-resistant colonies were screened for positive clones.

A cracking gel procedure (Promega Protocols and Applications Guide, 19991) was used to screen out the positive clones. The identity of the correct clones was further verified by BamHI/DraIII double digestion. The plasmid DNA obtained from the ampicillin-resistant colonies were digested by BamHI/HindIII and EcoRI/HindIII restriction endonucleases to verify the presence of human and mouse $IgG_1$ RT-PCR fragments, respectively. The resulting pcDNA3.1(−)-based human and mouse $IgG_1$ intermediate cloning vectors were named pcDNA3.1(−)-hIgG$_1$ and pcDNA3.1(−)-mIgG$_1$, respectively.

Characterization and localization of the fusion proteins

Transfected cells express fairly high levels of intact hTR-FcΔH(SEQ ID NO:4). BHK cells also expressed hTR-Fc and hTR-FcΔCH$_1$ (SEQ ID NO:2) that were shown to have approximately the expected molecular mass. The transfection of baby hamster kidney (BHK) cells was performed by plating on 6-well tissue culture plates (Fisher Scientific, Pittsburgh, Pa.) or Lab-Tek chamber slides (Nunc, Napierville, Ill.) coated with poly-ornithine (Sigma, St. Louis, Mo.). Cells were transfected using the calcium phosphate-based Stable Transfection Kit (Stratagene, San Diego, Calif.), using 1.0 mg DNA per ml of media per well. Cells were transfected for 6–8 hours and grown for two days in Dulbecco's Modified Essential Medium (DMEM) with 10% heat inactivated fetal bovine serum (FBS). Polyclonal and monoclonal stable cell lines were selected using G418 (Gibco-BRL, Gaithersburg, Md.) at a concentration of 1.0 mg/ml and maintained at 0.25 mg/ml.

Expression and localization of reverse Fc by Western blot, immunostaining, and ELISA Western blot analysis was used to determine relative hTR-Fc expression. Transfected cells were lysed directly in hot Laemmli sample buffer. The lysates were resolved by SDS-PAGE and immunoblotted using goat anti-human IgG Fc specific HRP (horseradish peroxidase)-conjugated antibody diluted 1:5000 (Sigma, St. Louis MO). Specific bands were visualized by chemiluminescence (Pierce, Rockford, Ill.).

To determine if hTR-FcΔH (SEQ ID NO:4) targeted to the plasma membrane in the desired orientation, surface expression of reverse human IgG Fc was monitored by both immunostaining and ELISA. For immunofluorescence staining, cells were processed essentially as described by Richards et. al. (*J Cell Biol*, 134:1157–68, 1996). Chimeric hTR-Fc molecules were visualized using goat anti-human IgG Fc specific Cγ3 (carbocyanine) linked antibody (Jackson ImmunoResearch, West Grove, Pa.) diluted at 1:1000. Nuclei were visualized by DAPI staining.

A stable BHK cell line expressing hTR-FcΔH (SEQ ID NO:4) produced high levels of the reversed Fc, while wild-type cells exhibited no observable signal. Similar membrane targeting was seen with the CH$_1$-deletion mutant (hTR-FcΔCH$_1$; SEQ ID NO:2), whereas intact IgG Fc with only Fab deletion (hTR-Fc) targeted to the endoplasmic reticulum almost exclusively.

Surface expression of reverse Fc was semi-quantitated by ELISA. For ELISA, cells were seeded at 100,000/well in a 96-well tissue culture plate, as described by Margulies (In: *Current Protocols in Immunology*, Vol. 1, 1st Edition, Coligan et al., eds., John Wiley & Sons, Inc, 1994, p. 2.1.13). Goat anti-human IgG Fc alkaline phosphatase conjugate (Sigma, St. Louis Mo.) was added at 1:1000 dilution. Substrate PNPP was added and the plate was read after 30 minutes at $OD_{405}$ nm on a ThermoMax Plate reader (Molecular Devices, Menlo Park, Calif.).

Cell surface-expressed human $IgG_1$ Fc from cells which showed positive surface immunofluorescence was monitored by ELISA. Transfected cells exhibited a very high signal versus wild-type BHK cells, which showed a near background signal (FIG. 2). These results confirm that the transformed hTR-FcΔH (SEQ ID NO:4) cells express high levels of human Fc on the cell surface, consistent with the immunofluorescent data.

Characterization of cell surface expressed reverse Fc fusion proteins

To prove the design, immune complexes were created using BHK cells and anti-BHK antibodies. The effect of opsonized BHK cells on superoxide production by mouse macrophages were examined and the results are presented in FIG. 3A. Preparation of mouse macrophages was performed as follows: Macrophages were elicited by thioglycollate broth in nude mice (N:NIH(s)-nu/nuDF (Taconic Farms, Germantown, N.Y.). Mouse peritoneal macrophages were collected 72 hours after thioglycollate broth injection and resuspended into $5 \times 10^6$ cells/ml in RPMI+10% FCS. Fifty ml per well of cells were seeded in a 96-well tissue culture plate and the plate was incubated at 37° C. for at least 3 hours. The non-adherent cells were removed by washing three time with HBSS and 50 ml/well of HBSS were added.

BHK cells opsonized with different concentrations of antibodies produced a dose-dependent increase in superoxide production, while control cells alone had no effect.

Various hTR-Fc fusion proteins (hTR-Fc, hTR-FcΔCH$_1$ [SEQ ID NO:2] and hTR-FcΔH [SEQ ID NO:4]) were expressed transiently or stably in BHK cells. The stable clones were derived from hTR-FcΔCH$_1$ [SEQ ID NO:1]and hTR-FcΔH [SEQ ID NO:3] transfected polyclonal cells, and the effect of these clones on superoxide production by mouse macrophages are shown in FIG. 3B. All subclones induced superoxide production. hTR-Fc did not express cell surface Fc therefore was eliminated from the study. BHK-FcΔH clone 3 was chosen for further characterization.

Functional analysis of BHK-FcΔH (3)

To assess whether cell surface expression of reverse Fc was biologically active in terms of Fc receptor binding and complement fixation, Fc receptor-mediated superoxide production in the human monocyte-like cell line was examined. Superoxide was measured spectrophotometrically as a function of the cell's ability to reduce cytochrome c. Superoxide production was determined using the 96-well microtiter plate assay of Tao et al. (*J Leukoc Biol*, 58: 203–8, 1995). 25,000 cells/well of either BHK-WT (control), opsonized BHK cells, or BHK-reverse Fc clones were added to the assay plate containing either human monocyte-like U937 cells (ATCC, Rockville, Md.) pre treated with recombinant human interferon-γ (R&D Systems, Minneapolis, Minn.) or lavaged mouse peritoneal macrophages. The $O_2$-release was measured as the superoxide dismutase (SOD) inhibitable reduction of cytochrome c at 550 nm by using a ThermoMax Plate reader (Molecular Devices, Menlo Park, Calif.). The rate of $O_2$-production was monitored from time 0 to 60 mm after stimulation.

BHK-FcΔH(3) cells induced an increase in superoxide production, while wild-type cells had no effect.

Figure 4:
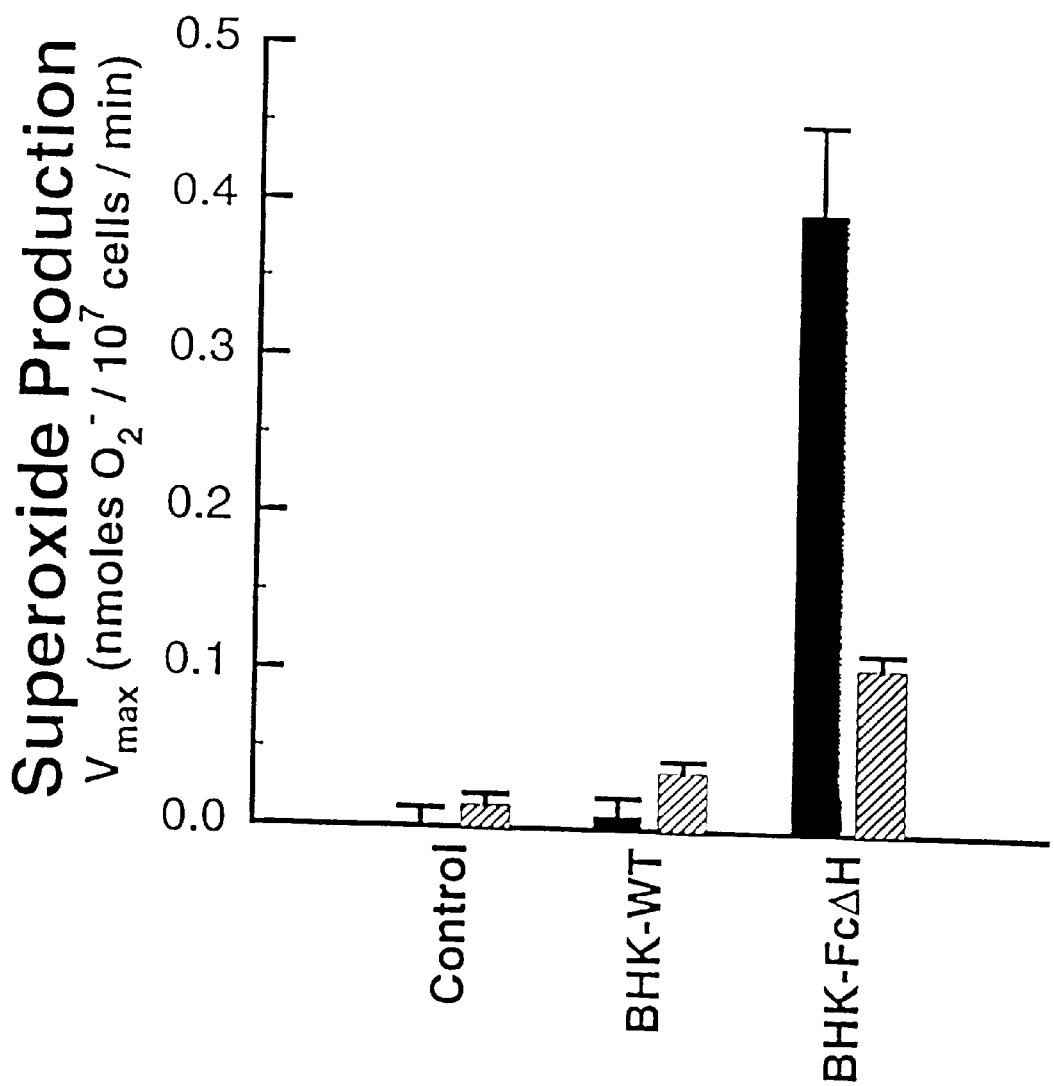
FIG. 4 shows the effect of anti-FCγR1 mAb F(ab')$_2$ on BHK-FcΔH-induced (SEQ ID NO:4) superoxide production in U937 cells. The solid bar represents superoxide assay conditions without anti-FCγR1 mAb treatment, and the shaded bar represents assay conditions with anti-FCγR1 mAb pretreatment.

Addition of FcγRI receptor specific antibody almost completely blocked this induction (FIG. 4), indicating that the observed macrophage activation was specifically mediated by FcγRI. Furthermore, superoxide production induced by BHK-FcΔH is dose-dependent. [Pre-incubation of U937 cells with anti-CD64 F(ab')2, a monoclonal antibody specific for human FcγRI, almost completely abolished BHK-FcΔH induced superoxide production (FIG. 4).]

The ability of cells expressing reverse Fc to activate complement

The ability of cells expressing reverse Fc to activate complement was also examined. In a C3a enzyme immunoassays, BHK-FcΔH cells failed to activate complement, although immune complexes (IC) containing intact IgG activated complement effectively (FIG. 5). For the C3a enzyme immunoassay, the effect of BHK-WT and BHK-IgGΔH on complement activation was evaluated using QUIDEL C3a Enzyme Immunoassay kit (QUIDEL, San Diego, Calif.). Human serum opsonized zymosan (immune complexes) was used as a positive control. All specimen handling was carried out according to the guidelines provided by the manufacture. Human serum (complement) was incubated with BHK-WT, BHK-IgGΔH or immune complexes for 1 hour at 37° C. Then serum samples were collected and subject to C3a-desArg quantitation. All calculations were made from a standard curve provided by the manufacturer.

Other C3a enzyme immunoassays can be performed as described by Burger et al. (*J Immunol*, 141: 553–8, 1988); Mollnes et al. (*Olin Exp Immunol*, 73: 484–8, 1988); and Hugh (In *Laboratory and Research Methods in biology and Medicine*, Nakamura et al., Eds., New York, 1988, p. 443).

Complement Dependent Cytotoxicity.

BHK wild type (BHK-WT) and BHK-FcΔH (SEQ ID NO:4) cells were used as target cells in an ADCC assay. All testing samples were set up in two groups of triplicates and assayed employing a standard National Institutes of Health (NIH) tissue typing technique (American Society for Histocompatibility and Immunogenetics (ASHI) Manual, 1994). One group of triplicates was analyzed with sheep hypersensitized serum and BHK-WT cells, while the second group of triplicates was assayed in the same manner with the addition of exogenously prescreened rabbit complement. In the case of BHK-FcΔH, the assay was performed in the absence or presence of exogenous prescreened rabbit complement. Samples were prepared using a two-color immunofluorescent microcytotoxic analysis procedure. An one-hour incubation of 1 ml sheep serum and 1 ml containing 1,000 BHK cells was followed by a second one-hour incubation with or without additional 5 ml rabbit complement. In the same microtiter well, the percentage of living cells (negative reactivity) was visualized using fluorescein diacetate, while the percentage of dead cells (positive reactivity) was visualized using propidium iodide. All serum specimens were set up in 1:2 serial dilution to a maximum of a 1:100,000 dilution. All data was scored using a Nikon Diaphot™ inverted fluorescence microscope with a 488 nm wavelength excitation.

In an ADCC assay containing BHK-WT or BHK-FcΔH (SEQ ID NO:4), no cell lysis was observed in the presence of complement (TABLE 1), whereas anti-BHK sensitized serum (containing intact IgG) effectively lysed BHK target cells. These results suggest that although a high level of Fc was expressed on the cell surface, the chimera of IgG$_1$ heavy chain with CH$_1$ deletion or CH$_1$ and hinge deletion did not activate complement, despite being a potent stimulus for macrophages.

TABLE 1

| Cell Type | Cell Surface Fc (OD$_{405}$) | CDC + complement |
|---|---|---|
| BHK-WT | 0.291 ± 0.052 | |
| BHK-FcΔH | 2.803 ± 0.283 | |

These results suggest that Fc expressed on the cell surface in a reversed orientation can activate macrophages, and the observed activation is mediated specifically through Fc receptors. The IgG$_1$ heavy chain with CH$_1$ deletion (SEQ ID NO:2) or CH₁-hinge deletion (SEQ ID NO:4) gave similar levels of macrophage activation. The extracellular region of the transferrin receptor used to anchor Fc (residues 89–97) is able to substitute for native hinge. The hTR fragment used in this study is approximately equal in length, if not amino acid identity, to native IgG₁ hinge, and may effectively provide functions similar to that of the hinge region. Another critical function of hinge is to provide intermolecular disulfide bonds between heavy and light chains using critical cysteine residues. The hTR (1-97), which contains at least one cysteine (C89) necessary for TR dimerization, is able to mimic hinge by allowing multimer association of the hTR-FcΔH monomers.

In summary, a novel human IgG₁ Fc chimera has been constructed and the chimeric polypeptide was successfully expressed on the cell surface, in a reversed orientation. The Fc receptor binding property was retained in the molecule, IgG₁ Fc chimera the complement activation capability was absent.

EXAMPLE 2

ENCAPSULATION PROCEDURE

Transformed cells from EXAMPLE 1 are encapsulated for transplantation in a host. The encapsulated cell devices typically include:

1) a semipermeable polyether sulfone (PES) hollow fiber membrane fabricated by AKZO Nobel Faser AG;
2) a hub membrane segment;
3) a light cured methacrylate (LCM) resin leading end; and
4) a silicone tether.

The morphology of the device is as follows: The inner surface has a permselective skin. The wall has an open cell foam structure. The outer surface has an open structure, with pores up to 1.5 µm occupying 30±5% of the outer surface. Hollow fibers are fabricated from PES with an outside diameter of 720 mm and a wall thickness of 100 mm (AKZO-Nobel Wippertal, Germany). These fibers are described in U.S. Pat. Nos. 4,976,859 and 4,968,733. A PES#5 membrane, which has a MWGO of about 280 kilodalton (kDa), is sometimes used. A PES#8 membrane, which has a MWGO of about 90 kDa, is at other times used. The semipermeable PES membranes typically have the following characteristics:

| Internal Diameter | 500 ± 30 µm |
|---|---|
| Wall Thickness | 100 ± 15 µm |
| Force at Break | 100 ± 15 cN |
| Elongation at Break | 44 ± 10% |
| Hydraulic Permeability | 63 ± 8 (ml/mn m² min Hg) |
| nMWGO (dextrans) | 280 ± 20 kDa |

The components of the device are commercially available. The LCM glue is available from Ablestik Laboratories (Newark, Del.); Luxtrak Adhesives LCM23 and LGM24). The tether material is available from Specialty Silicone Fabricators (Robles, Ga.). The tether dimensions are 0.79 mm OD×0.43 mm ID×length 202 mm.

The encapsulation procedure is as follows: Fiber material is first cut into 5 cm long segments and the distal extremity of each segment sealed with a photopolymerized acrylic glue (LCM-25, ICI). Following sterilization with ethylene oxide and outgassing, the fiber segments are loaded with a suspension of about $2 \times 10^5$ transfected cells in a collagen solution (Zyderm® soluble bovine collagen) by a Hamilton syringe and a 25 gauge needle through an attached injection port. The proximal end of the capsule was sealed with the same acrylic glue. Sometimes, the collagen matrix was Zyplast®. The volume of the device for human use is approximately 15–18 µl.

A silicone tether (Specialty Silicone Fabrication, Taunton, Mass.) (ID: 690 µm; OD: 1.25 mm) is placed over the proximal end of the fiber allowing easy manipulation and retrieval of the device.

The foregoing description has been presented only for the purposes of illustration and is not intended to limit the invention to the precise form disclosed, but by the claims appended hereto.

What is claimed is:

1. A cell transformed in vitro comprising a vector, said vector comprising a promoter operatively linked to a polynucleotide sequence encoding a fusion protein comprising the Fc portion of an IgG molecule linked at the amino terminus to the transferrin receptor hinge region, wherein upon expression, the fusion protein is expressed on the cell surface.

2. The cell according to claim 1, wherein the cell is a human cell.

3. The cell according to claim 1, wherein the cell is a rodent cell.

4. The cell according to claim 3, wherein the rodent cell is a mouse cell.

5. A vector comprising a promoter operatively linked to a polynucleotide sequence encoding a fusion protein comprising the Fc portion of an IgG molecule linked at the amino terminus to the transferrin receptor hinge region.

6. A composition comprising:
   (a) a plurality of cells according to claim 1; and
   (b) a jacket surrounding the plurality of cells, wherein the jacket comprises a permselective membrane.

* * * * *